| United States Patent [19] | [11] Patent Number: 4,740,632 |
| Anderson et al. | [45] Date of Patent: Apr. 26, 1988 |

[54] PROCESS FOR REMOVING METHANOL FROM ALKYLATION UNIT FEED STREAM

[75] Inventors: Ardis L. Anderson; David A. Strah, both of Ponca City, Okla.

[73] Assignee: Conoco Inc., Ponca City, Okla.

[21] Appl. No.: 4,015

[22] Filed: Jan. 16, 1987

[51] Int. Cl.$^4$ .......................... C07C 41/06; C07C 7/10
[52] U.S. Cl. ...................................... 568/697; 568/699; 585/331; 585/835
[58] Field of Search ............... 568/697, 698; 585/835, 585/331

[56] References Cited

U.S. PATENT DOCUMENTS

| 3,453,343 | 7/1969 | Holiday | 260/676 |
| 3,511,596 | 5/1970 | Adler et al. | 23/2 |
| 4,383,893 | 5/1983 | Kaibel et al. | 203/35 |
| 4,465,870 | 8/1984 | Herskovits | 568/697 |
| 4,490,563 | 12/1984 | Van Pool et al. | 568/697 |

FOREIGN PATENT DOCUMENTS

| 2705538 | 8/1978 | Fed. Rep. of Germany . |
| 693762 | 7/1953 | United Kingdom . |
| 786303 | 11/1957 | United Kingdom . |

*Primary Examiner*—Howard T. Mars

[57] ABSTRACT

A process of removing methanol from a mixed stream comprising methanol and at least one hydrocarbon and utilizing the hydrocarbon as feed for an acid catalyzed alkylation unit which produces a spent acid stream is provided. The process is comprised of the steps of contacting the mixed stream with at least a portion of the alkylation unit spent acid stream whereby the methanol is reacted therewith and an aqueous reaction mixture is formed, separating the aqueous reaction mixture from the hydrocarbon and conducting the hydrocarbon to the alkylation unit.

11 Claims, 1 Drawing Sheet

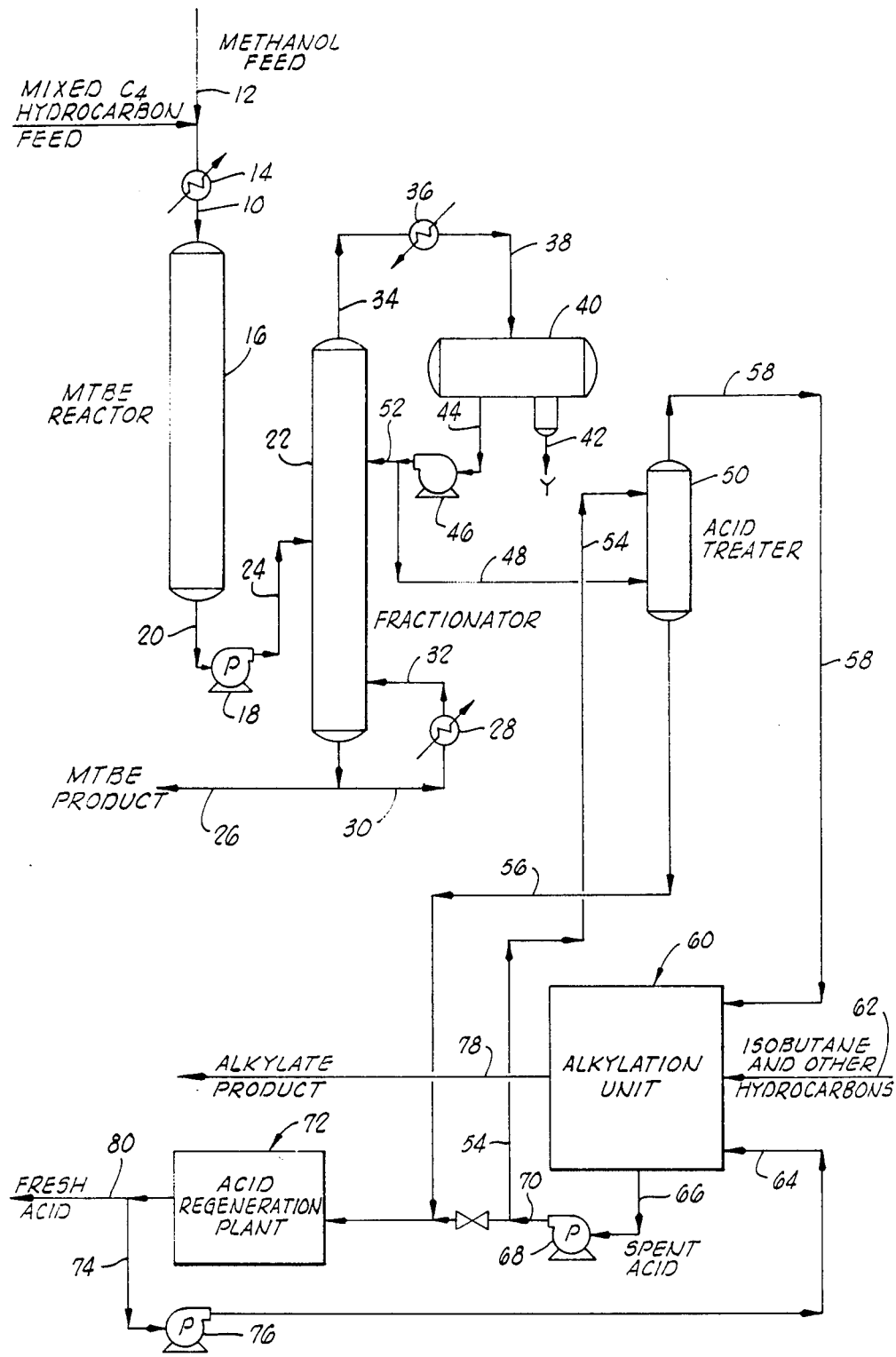

PROCESS FOR REMOVING METHANOL FROM ALKYLATION UNIT FEED STREAM

BACKGROUND OF THE INVENTION

1. Field of the Invention

This invention relates generally to a process for removing methanol from an alkylation unit feed stream, and more particularly, to a process for removing methanol from the hydrocarbon phase produced in the fractionation of an MTBE reaction mixture whereby the hydrocarbon phase can be utilized as an alkylation unit feed.

2. Description of the Prior Art

In producing gasoline it has become desirable to utilize high octane blending components such as methyl tertiary butyl ether (MTBE) so that blends of unleaded gasoline can be of the required octane rating. MTBE is typically produced in a process wherein methanol is catalytically reacted with isobutene in a mixed $C_4$ hydrocarbon stream. The mixed $C_4$ hydrocarbon stream is commonly derived from conventional fluid catalytic cracking units and coking operations present in crude oil refineries.

In the MTBE production process, a stochiometric excess of methanol is mixed with the isobutene present in the mixed $C_4$ hydrocarbon stream in the presence of an acidic ion exchange catalyst such as AMBERLYST-15. AMBERLYST-15 is commercially available from the Rohm & Haas Company of Philadelphia, Pa. and is a cationic, strongly acidic, ion exchange resin containing a sulfonated polystyrene crosslinked with divinylbenzene. The excess of methanol is used to obtain a good conversion of isobutene and to suppress side reactions resulting in low octane polymers.

The catalytic alkylation of isobutane with olefins such as butenes is also a well known process utilized in refineries for producing high octane gasoline components. Generally, refinery alkylation units utilize a stream of acid as the catalyst and produce a spent acid stream.

While the unreacted $C_4$ hydrocarbon stream remaining after separation of produced MTBE therefrom has heretofore been charged to an alkylation unit as a feed stream thereto, because of the presence of methanol in the stream it has been necessary to subject the stream to a methanol removal process. That is, the presence of methanol in the alkylation unit hydrocarbon feed stream from the MTBE production process is detrimental to the alkylation unit since methanol reacts with isobutane and acid to produce undesired low octane compounds and catalyst diluting water.

The methanol removal processes heretofore utilized include adsorption and absorption processes. For example, U.S. Pat. No. 4,490,563 issued Dec. 25, 1984, describes a system which includes the water absorption of methanol to remove it from the unreacted $C_4$ effluent produced in an MTBE production and separation process. Such methanol removal processes have been used successfully, but they generally require relatively elaborate equipment and are expensive to carry out.

Thus, there is a need for a simple and inexpensive process for removing methanol from the MTBE production process unreacted hydrocarbon effluent prior to charging such effluent to an alkylation unit.

SUMMARY OF THE INVENTION

The present invention provides a process which fulfills the need described above, i.e., a simple and inexpensive process for removing methanol from an alkylation unit feed stream, particularly the mixed hydrocarbon feed stream emanating from an MTBE production process. The process basically comprises contacting the mixed hydrocarbon stream containing methanol with at least a portion of the spent acid catalyst stream produced in the alkylation unit whereby the methanol is reacted therewith and an aqueous reaction mixture is formed, separating the aqueous reaction mixture from the remaining hydrocarbon stream and conducting the hydrocarbon stream to the alkylation unit as a feed stream thereto.

In a more specific embodiment of the invention, an improved process for recovering MTBE from a reaction mixture comprising MTBE, methanol, and hydrocarbons, removing methanol therefrom and utilizing the hydrocarbons as feed to an acid catalyzed alkylation unit which produces a spent acid stream is provided. In the process, the MTBE reaction mixture is fractionated under conditions which separate an overhead stream comprising hydrocarbons, and methanol and a bottoms MTBE product stream substantially devoid of methanol. The overhead stream is condensed and then contacted with at least a portion of the alkylation unit spent acid stream whereby the methanol is reacted to form an aqueous reaction mixture. The aqueous reaction mixture is separated from the hydrocarbons and the resulting substantially methanol-free hydrocarbons are charged to the alkylation unit as a feed stream.

The aqueous spent acid reaction mixture separated from the hydrocarbons can be combined with other spent acid and regenerated to produce fresh acid for recycle as catalyst to the alkylation unit.

Thus, a principal object of the present invention is to provide a simple and economical process for removing methanol from an alkylation unit hydrocarbon feed stream. The process is particularly suitable for incorporation into a combined MTBE production and alkylation refinery system. Other and further objects, features and advantages of the invention will be readily apparent to those skilled in the art upon a reading of the description of preferred embodiments which follows when taken in conjunction with the accompanying drawing.

BRIEF DESCRIPTION OF THE DRAWING

The drawing forming a part of this disclosure is a schematic view of a system for carrying out the process of the present invention in association with an MTBE production process and an alkylation process.

DESCRIPTION OF PREFERRED EMBODIMENTS

As shown in the drawing, a mixed $C_4$ hydrocarbon feed stream is conducted by a conduit 10 to an MTBE reactor 16. Such feed in a refinery is typically comprised of isobutene and other $C_4$ hydrocarbons such as isobutane, normal butane, butene-1 and butene-2. A typical mixture contains about 10% or more of isobutene. The mixed $C_4$ hydrocarbon feed stream flowing through the conduit 10 is combined with a methanol feed stream by way of a conduit 12 connected to the conduit 10 whereby a stoichiometric excess of methanol to isobutene results. The combined feed streams are heated as they flow through a heat exchanger 14 disposed in the conduit 10. The heated combined feed is then introduced into the MTBE reactor 16 which contains an acidic ion exchange catalyst such as AMBERLYST-15.

The isobutene contained in the mixed $C_4$ hydrocarbons and the methanol react in the reactor 16 to form a reaction mixture comprising MTBE, methanol and unreacted $C_4$ hydrocarbons. The reaction mixture can also contain water as a result of the mixed $C_4$ hydrocarbon feed stream containing dissolved and entrained water therein. Some of the water may react with isobutene to produce tertiary butyl alcohol, another octane enhancer.

The reaction mixture is withdrawn from the reactor 16 and conducted to the inlet connection of a pump 18 by a conduit 20 connected therebetween. From the discharge of the pump 18, the mixture is conducted to the inlet connection of a fractionator 22 by a conduit 24. The reaction mixture is fractionated in the fractionator 22 under conditions which separate the reaction mixture into an overhead vapor stream comprised of hydrocarbons and methanol and a bottoms liquid stream comprised of substantially pure MTBE. The MTBE bottom stream is withdrawn from the fractionator 22 by way of a conduit 26 connected thereto with a portion of such stream being recycled through a reboiler 28 and back to the fractionator 22 by way of a conduit 30 connected between the conduit 26 and the reboiler 28 and a conduit 32 connected between the reboiler 28 and the fractionator 22.

The overhead vapor stream is withdrawn from the top of the fractionator 22 by way of a conduit 34 connected thereto. The conduit 34 leads the overhead vapor stream to a condensor 36 wherein it is condensed into a hydrocarbon phase containing some methanol and, if unreacted water is present, an aqueous phase comprised of water and methanol. The condensed overhead stream is coducted from the condensor 36 by a conduit 38 to a separator 40 wherein the hydrocarbon phase and aqueous phase (if any) are separated. The separated aqueous phase is withdrawn from the separator 40 by a conduit 42 which conducts it to a drain or point of further processing. The hydrocarbon phase comprised of hydrocarbons and methanol is withdrawn from the separator 40 by a conduit 44 which conducts it to the inlet connection of a pump 46. From the pump 46, a major portion of the hydrocarbon-methanol stream is pumped to an acid treater 50. A conduit 52 connected between the conduit 48 and an inlet connection of the fractionator 22 returns a minor portion of the hydrocarbon-methanol stream to the fractionator 22 as reflux.

The acid treater 50 can take various forms such as a vertical column, an in-line mixer connected to an accumulator-separator, or other similar apparatus for contacting the hydrocarbon stream with an aqueous spent acid stream and then separating the hydrocarbon and aqueous streams. While within the acid treater 50 the hydrocarbon-methanol stream is contacted with an aqueous spent acid stream conducted to the acid treater 50 by way of the conduit 54 connected thereto. Upon such contact, the methanol contained in the hydrocarbon-methanol stream reacts with the spent acid to form an aqueous reaction mixture which accumulates in the bottom portion of the acid treater 50 and is withdrawn therefrom by way of a conduit 56 connected thereto. The resulting substantially methanol devoid hydrocarbon stream accumulates in the top portion of the acid treater 50 and is withdrawn therefrom by a conduit 58 connected thereto. The conduit 58 leads the hydrocarbon stream to a conventional refinery alkylation unit generally designated by the numeral 60. In addition to the purified hydrocarbon stream conducted to the alkylation unit 60 by the conduit 58, an isobutane feed stream is conducted thereto by way of a conduit 62. A continuous stream of catalyst comprised of an aqueous acid solution, generally a sulfuric acid solution, is conducted to the alkylation unit 60 by way of a conduit 64 attached thereto. A spent acid stream produced by the alkylation unit 60 is withdrawn therefrom by way of a conduit 66 connected thereto. The conduit 66 conducts the spent acid stream to the inlet connection of a pump 68, the discharge connection of which is connected by a conduit 70 to an acid regeneration plant, generally designated by the numeral 72. The conduits 54 and 56, previously described, are connected to the conduit 70 at points upstream and downstream of a flow control valve 55 disposed therein, respectively. Fresh acid produced by the plant 72 is recycled to the alkylation unit 60 by way of a conduit 74 and pump 76 connected to the conduit 64.

At least a portion of the spent acid stream flowing through the conduit 70 is diverted by way of the conduit 54 connected thereto to the acid treater 50. The aqueous reaction mixture withdrawn from the acid treater 50 by way of the conduit 56 is conducted back to the conduit 70 from where it flows along with other spent acid to the acid regeneration plant 72. Alkylate product produced in the alkylation unit 60 is withdrawn therefrom by way of a conduit 78 connected thereto and excess fresh sulfuric acid produced by the acid regeneration plant is conducted to a storage or other facility by a conduit 80 connected to the conduit 74.

The spent acid produced in a typical alkylation unit is an aqueous solution which contains active sulfuric acid in a concentration in the range of from about 86% to about 92% by weight of the solution. For each mole of methanol present in the mixed hydrocarbon-methanol stream from which methanol is to be removed, one mole of sulfuric acid is required for reaction therewith in accordance with the following equation:

$$CH_3OH + H_2SO_4 \rightarrow CH_3HSO_4 + H_2O$$

Thus, the process of the present invention for removing methanol from a mixed stream comprising methanol and at least one hydrocarbon, and then utilizing the resulting substantially methanol devoid hydrocarbon stream as feed to an acid catalyzed alkylation unit includes the steps of contacting the mixed stream with at least a portion of the spent acid stream produced by the alkylation unit whereby the methanol is reacted therewith and an aqueous reaction mixture is formed, separating the aqueous reaction mixture from the remaining hydrocarbon stream, and conducting the hydrocarbon stream to the alkylation unit.

In the usual case the mixed stream is comprised of methanol and various $C_4$ hydrocarbons, e.g., isobutene and other $C_4$ hydrocarbons produced in the fractionation recovery of MTBE. Also, in the usual case, the acid catalyst utilized in the alkylation unit is an aqueous sulfuric acid solution and a spent sulfuric acid solution having an average concentration of active sulfuric acid of about 90% by weight of the solution is produced by the alkylation unit.

In order to further illustrate the process of the present invention, the following example is given:

EXAMPLE

The mixed hydrocarbon-methanol stream which is conducted to the acid treater 50 by way of the conduit 48 contains about 1% by weight methanol and has a flow rate of about 30,000 lbs/hr. 1,020 lbs/hr of a spent sulfuric acid catalyst solution containing about 90% by weight active sulfuric acid are conducted to the treater 50 by way of the conduit 54. The active sulfuric acid in the spent acid solution reacts with the methanol in the mixed hydrocarbon-methanol stream. Upon separation of the aqueous phase from the hydrocarbon phase in the treater 50 and the withdrawal of the hydrocarbon phase therefrom, it contains less than about 0.005% by weight methanol.

From the foregoing description, one skilled in the art can easily ascertain the essential characteristics and steps of this invention, and without departing from the spirit and scope thereof, can make various changes and modifications to adapt the invention to various usages and conditions.

What is claimed is:

1. A process of removing methanol from a mixed stream comprising methanol and at least one hydrocarbon and utilizing the resulting substantially methanol devoid hydrocarbon stream as feed to an acid catalyzed alkylation unit which produces a spent acid stream comprising the steps of:
   contacting said mixed stream with at least a portion of said alkylation unit spent acid stream whereby said methanol is reacted therewith and an aqueous reaction mixture is formed;
   separating said aqueous reaction mixture from the remaining hydrocarbon stream; and
   conducting said hydrocarbon stream to said alkylation unit.

2. The process of claim 1 wherein said mixed stream is comprised of methanol and various $C_4$ hydrocarbons.

3. The process of claim 1 wherein said mixed stream is the overhead condensed hydrocarbon phase comprising methanol, isobutene and other $C_4$ hydrocarbons produced in the fractionation recovery of MTBE from an MTBE reaction effluent.

4. The process of claim 3 wherein said spent acid is spent sulfuric acid.

5. The process of claim 4 wherein said spent sulfuric acid stream contains in the range of from about 86% to about 92% by weight active sulfuric acid.

6. The process of claim 5 wherein said mixed stream is contacted with said spent sulfuric acid stream in a 1:1 mole ratio of active sulfuric acid to methanol.

7. A process for recovering MTBE from a reaction mixture containing MTBE, methanol and hydrocarbons, removing methanol therefrom and utilizing the hydrocarbons as feed to a sulfuric acid catalyzed alkylation unit which produces a spent sulfuric acid stream comprising the steps of:
   fractionating said reaction mixture under conditions which separate an overhead stream comprised of hydrocarbons and methanol and a bottoms stream comprising MTBE substantially devoid of methanol;
   condensing said overhead stream into a hydrocarbon phase containing some methanol;
   contacting said hydrocarbon phase with at least a portion of said alkylation unit spent sulfuric acid stream whereby methanol contained in said hydrocarbon phase is reacted with said spent sulfuric acid to form an aqueous reaction mixture therein;
   separating said aqueous reaction mixture from said hydrocarbon phase; and
   conducting said hydrocarbon phase to said alkylation unit.

8. The process of claim 7 wherein said hydrocarbons are comprised of isobutene and other $C_4$ hydrocarbons.

9. The process of claim 7 wherein said reaction mixture is formed by reacting a hydrocarbon mixture comprised of isobutene and other $C_4$ hydrocarbons and water with methanol in the presence of an acidic ion exchange type catalyst.

10. The process of claim 9 wherein said spent sulfuric acid stream contains in the range of from about 86% to about 92% by weight active sulfuric acid.

11. The process of claim 10 wherein said mixed stream is contacted with said spent sulfuric acid stream in a 1:1 mole ratio of active sulfuric acid to methanol.

* * * * *